United States Patent
Bond et al.

(10) Patent No.: US 11,739,362 B2
(45) Date of Patent: Aug. 29, 2023

(54) COLOUR CHANGING COMPOSITIONS

(71) Applicant: FRESH CHECK LTD., London (GB)

(72) Inventors: Alexander Bond, London (GB); John Simpson, London (GB); Robert Peach, London (GB)

(73) Assignee: FRESH CHECK LTD., London (GB)

( * ) Notice: Subject to any disclaimer, the term of this patent is extended or adjusted under 35 U.S.C. 154(b) by 854 days.

(21) Appl. No.: 16/500,094

(22) PCT Filed: Apr. 4, 2018

(86) PCT No.: PCT/GB2018/050913
§ 371 (c)(1),
(2) Date: Oct. 1, 2019

(87) PCT Pub. No.: WO2018/185486
PCT Pub. Date: Oct. 11, 2018

(65) Prior Publication Data
US 2021/0068394 A1    Mar. 11, 2021

(30) Foreign Application Priority Data
Apr. 4, 2017 (GB) .................................. 1705407

(51) Int. Cl.
| | | |
|---|---|---|
| G01N 21/78 | (2006.01) | |
| G01N 21/80 | (2006.01) | |
| A01N 33/12 | (2006.01) | |
| C12Q 1/04 | (2006.01) | |

(52) U.S. Cl.
CPC ............... *C12Q 1/04* (2013.01); *A01N 33/12* (2013.01); *G01N 21/78* (2013.01); *G01N 21/80* (2013.01); *C12Q 2304/00* (2013.01)

(58) Field of Classification Search
CPC .......... G01N 21/78; G01N 21/80; C12Q 1/04; A01N 33/12
See application file for complete search history.

(56) References Cited

U.S. PATENT DOCUMENTS

| | | |
|---|---|---|
| 3,067,015 A | 12/1962 | Lawdermilt |
| 5,053,339 A | 10/1991 | Patel |
| 5,306,466 A | 4/1994 | Goldsmith et al. |
| 5,443,987 A | 8/1995 | Decicco et al. |

(Continued)

FOREIGN PATENT DOCUMENTS

| | | |
|---|---|---|
| CN | 101434565 A | 5/2009 |
| CN | 101805778 A | 8/2010 |

(Continued)

OTHER PUBLICATIONS

Schwyn et al., "Universal Chemical Assay for the Detection and Determination of Siderophores", Anal Biochem. Jan. 1987; 160(1): 47-56.

(Continued)

*Primary Examiner* — Brian R Gordon
*Assistant Examiner* — Dwan A Gerido
(74) *Attorney, Agent, or Firm* — Squire Patton Boggs (US) LLP

(57) ABSTRACT

The present invention relates to compositions comprising a metal, a metal aggregation inhibitor, and a colour changing agent. The metal is bindable to the colour changing agent to provide a change in colour on binding and/or release thereof.

34 Claims, 1 Drawing Sheet

(56) References Cited

U.S. PATENT DOCUMENTS

| | | | |
|---|---|---|---|
| 5,650,331 | A | 7/1997 | Jorgensen et al. |
| 5,766,607 | A | 6/1998 | Fenwick et al. |
| 5,998,161 | A | 12/1999 | Caillouette |
| 6,086,967 | A | 7/2000 | Whiteman et al. |
| 6,270,724 | B1 | 8/2001 | Woodaman |
| 6,479,016 | B1 | 11/2002 | Goldsmith et al. |
| 6,593,142 | B2 | 7/2003 | Kelly et al. |
| 6,924,147 | B2 | 8/2005 | Kelly et al. |
| 7,531,319 | B2 | 5/2009 | Martin et al. |
| 7,770,534 | B2 | 8/2010 | Cooperman |
| 8,637,657 | B2 | 1/2014 | Heinrichs et al. |
| 2004/0026544 | A1 | 2/2004 | Williams et al. |
| 2004/0115319 | A1 | 6/2004 | Morris et al. |
| 2005/0153052 | A1 | 7/2005 | Williams et al. |
| 2005/0153452 | A1 | 7/2005 | Williams et al. |
| 2005/0266574 | A1* | 12/2005 | Kosaka ................. G01N 33/70 436/86 |
| 2006/0057022 | A1 | 3/2006 | Williams et al. |
| 2006/0121165 | A1 | 6/2006 | Morris |
| 2006/0134613 | A1 | 6/2006 | Martin et al. |
| 2006/0134728 | A1 | 6/2006 | Macdonald et al. |
| 2007/0176773 | A1 | 8/2007 | Smolander et al. |
| 2007/0249012 | A1 | 10/2007 | Lye et al. |
| 2009/0176673 | A1 | 7/2009 | Hanes |
| 2010/0209521 | A1 | 8/2010 | Schalkhammer |
| 2010/0248299 | A1* | 9/2010 | Lye ........................ C12Q 1/04 435/34 |
| 2011/0245321 | A1 | 10/2011 | Heinrichs et al. |
| 2014/0313055 | A1 | 10/2014 | Warkentin et al. |
| 2015/0056333 | A1* | 2/2015 | Chaves Noguera ..... C12Q 1/04 426/87 |
| 2016/0011164 | A1 | 1/2016 | Chaves Noguera et al. |

FOREIGN PATENT DOCUMENTS

| | | |
|---|---|---|
| CN | 103499574 A | 1/2014 |
| CN | 104178440 A | 12/2014 |
| CN | 104894035 A | 9/2015 |
| EP | 0577092 A2 | 1/1994 |
| IN | 256586 | 7/2013 |
| JP | 2000-186274 A | 7/2000 |
| WO | WO 1995/033991 | 12/1995 |
| WO | WO 2001/086289 A1 | 11/2001 |
| WO | WO 2006/024848 | 3/2006 |
| WO | WO 2006/062870 A2 | 6/2006 |
| WO | WO 2009/059751 A1 | 5/2009 |
| WO | WO 2009/115533 | 9/2009 |
| WO | WO 2015/112679 A1 | 7/2015 |
| WO | WO 2015/118516 A1 | 8/2015 |

OTHER PUBLICATIONS

International Search Report and Written Opinion dated Jun. 6, 2018, in International Patent Application No. PCT/GB2018/050913, 9 pages.

Search Report dated Jan. 17, 2018, in UK Patent Application No. GB 1705407.3, 4 pages.

International Search Report for international application WO 2018/185486 A1; 2 pages.

Indian Office Action for patent application No. 201917037508 dated Jun. 11, 2021; 6 pages.

"Foodsniffer" from—http://www.myfoodsniffer.com/ dated Mar. 23, 2020 and May 1, 2020; 12 pages.

Ernvall, "Sensor detects spoilage of food", VTT Technical Research Centre of Finland, May 6, 2015, retrieved Mar. 23, 2020 from https://phys.org/news/2015-05-sensor-spoilage-food.html; 2 pages.

Jacobovitz, "A Colorimetric Sensor of Food Spoilage Based on a Molecularly Imprinted Polymer", Reference#: P01491, Johns Hopkins University Applied Physics Laboratory, 2014; 1 page.

MIMICA from https://www.mimicalab.com/dated Mar. 23, 2020; 4 pages.

Whitworth, "Detecting food spoilage with optical sensor", Last updated on Jan. 21, 2014; https://www.foodnavigator.com/Article/2014/01/21/CheckPack-optical-sensor-for-food-pr . . . Mar. 23, 2020; 4 pages.

* cited by examiner

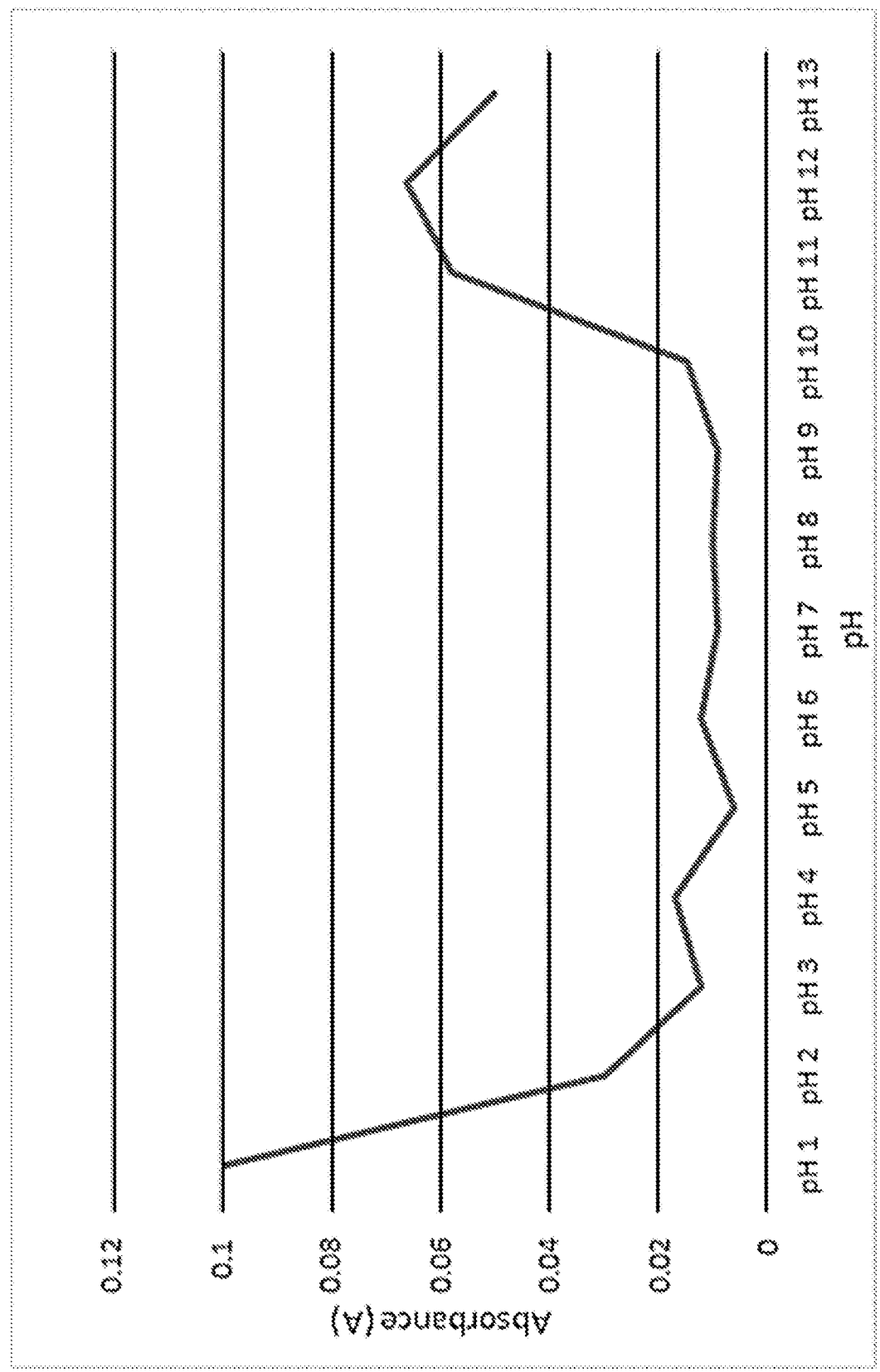

COLOUR CHANGING COMPOSITIONS

CROSS-REFERENCE TO RELATED APPLICATIONS

This application is a National Stage filing under 35 U.S.C. § 371 of International Patent Application No. PCT/GB2018/050913, filed Apr. 4, 2018 and entitled "COLOUR CHANGING COMPOSITIONS," which claims the benefit of and priority to GB Application No. 1705407.3, filed Apr. 4, 2017, both applications of which are herein incorporated by reference in their entirety for all purposes.

FIELD OF THE INVENTION

The present invention relates to compositions, a substrate comprising a composition and a label comprising a composition. The invention has particular, but not exclusive, application in the detection, reduction and/or elimination of microorganisms, such as bacteria. The invention also has particular, but not exclusive, application in the detection of chemical changes, such as pH.

BACKGROUND

Microorganisms, such as bacteria, typically require metal species (e.g. iron), for a number of biological processes. Bacteria typically extract iron from the ambient environment by means of iron-chelating compounds known as siderophores (e.g. enterobactin). Siderophores secreted by bacteria have high iron ($Fe^{3+}$) binding affinity and are thereby able to sequester ambient iron. After sequestration, the iron bound to the siderophore can be taken up by the bacteria using active transport mechanisms.

Chromeazurol S (CAS) is a colour changing agent which provides a change in colour upon binding and/or release of iron (blue on binding, orange on release/in unbound form). Due to a high iron binding affinity, when CAS with bound iron is exposed to siderophores, the iron is released from the CAS and instead binds preferentially to the siderophores, thereby resulting in a colour change in the CAS.

Levels of bacteria present in a sample are related to the amount of siderophore present in that sample, and the amount of siderophore present is related to the amount of iron that can be sequestered. Similarly, the colour change resulting from binding and/or release of iron is related to the amount of iron bound and/or released. Therefore, the colour change resulting from release of iron bound to CAS may be used to determine the amount of bacteria present in a sample.

Other microorganisms adopt similar techniques for iron uptake, and other metals can be sequestered in the same manner.

In many environments, it is desirable to reduce or eliminate microorganisms, and thereby to reduce or eliminate risk of infection to living organisms.

Exposure of CAS to certain chemical environments also causes release of iron, resulting in a colour change in the CAS. By way of example, CAS may have a different binding affinity for iron when in an acidic environment to that when in a basic environment.

It is desirable to provide an improved technique for reducing or eliminating microorganisms, and/or to provide an improved microorganism detection technique, and/or an improved technique for detecting certain chemical environments, and/or otherwise to obviate and/or mitigate one or more of the disadvantages with known techniques, whether identified herein or otherwise.

SUMMARY

According to a first aspect of the present invention, there is provided a sprayable composition comprising:
  a metal;
  a metal aggregation inhibitor;
  a colour changing agent;
  a surfactant; and
  a liquid vehicle;
  wherein the metal is bindable to the colour changing agent to provide a change in colour on binding and/or release thereof.

According to a second aspect of the present invention, there is provided a composition comprising:
  a metal;
  a metal aggregation inhibitor; and
  a colour changing agent;
  wherein the metal is bindable to the colour changing agent to provide a change in colour on binding and/or release thereof, and wherein the metal and colour changing agent are present at a molar ratio of about 1:1 to 15.

According to a third aspect of the present invention, there is provided substrate comprising a substrate carrier having a composition therein, wherein the composition comprises:
  a metal;
  a metal aggregation inhibitor; and
  a colour changing agent;
  wherein the metal is bindable to the colour changing agent to provide a change in colour on binding and/or release thereof.

According to a fourth aspect of the present invention, there is provided a label comprising a membrane, the membrane enveloping a composition and a carrier, the composition comprising:
  a metal;
  a metal aggregation inhibitor; and
  a colour changing agent,
  wherein the metal is bindable to the colour changing agent to provide a change in colour on binding and/or release thereof; wherein the membrane is impermeable to the colour changing agent to prevent passage therethrough, and wherein the membrane is permeable to siderophores to permit passage therethrough and to contact the colour changing agent.

According to a fifth aspect of the present invention there is provided a food and/or beverage container comprising a label according to the fourth aspect.

Definitions

The term "aliphatic", as used herein, means a substituted or unsubstituted straight-chain, branched or cyclic hydrocarbon, which is completely saturated or which contains one or more units of unsaturation, but which is not aromatic.

As used herein, the term "alkyl group" refers to both branched and straight chain, saturated aliphatic hydrocarbon radicals/groups.

As used herein, the term "substantially" is intended to modify a quality such that a given feature need not be "exactly" in accordance with that quality. Suitably, this modifier may indicate a deviation from the quality given of less than or equal to about 20%, such as less than or equal to about 15%, such as less than or equal to about 10%, such as less than or equal to about 5%, such as less than or equal to about 1%, such as about 0%. Generally speaking, lower deviation is preferred. By way of example, if a membrane is described as being substantially transparent in the visible spectrum, the membrane may be only about 80% transparent in the visible spectrum.

As used herein, the term "metal" is intended to include elemental forms or compounds of metals.

As used herein, the term "prevent passage" as applied to a particular component is intended to encompass both completely preventing passage and partially preventing passage (e.g. restraining/hindering passage), provided the passage does not materially affect the essential characteristics of that particular component.

By way of example, the membrane being impermeable to the colour changing agent to prevent passage thereof may encompass the membrane substantially preventing passage of the colour changing agent to the extent that a sufficient quantity of colour changing agent persists to effect a colour change upon binding and/or release of the metal.

Suitably, "prevent" may be understood to mean less than or equal to about 20% of the relevant component may pass through the membrane, on a weight basis (e.g. as measured over a period of about 1 month); such as less than or equal to about 15%, such as less than or equal to about 10%, such as less than or equal to about 5%, such as less than or equal to about 1%. Generally speaking, lower deviation is preferred, passage of about 0% is most preferred. The opposite definition applies to "permit passage" (i.e. encompassing both completely permitting and partially permitting).

As used herein, ratios may be defined as ranges of ratios, such as component A to component B being in a ratio of about 1:1 to 5. This should be understood to mean that component B may be present in a range from an equal amount of component A to five times the amount of component B.

DETAILED DESCRIPTION

According to a first aspect of the present invention, there is provided a sprayable composition comprising:
  a metal;
  a metal aggregation inhibitor;
  a colour changing agent;
  a surfactant; and
  a liquid vehicle;
  wherein the metal is bindable to the colour changing agent to provide a change in colour on binding and/or release thereof.

The composition of the present invention is useful in applications in which detection and reduction and/or elimination of microorganisms is desirable. The composition of the present invention can be sprayed onto an article (e.g. a surface) and used to detect the presence of microorganisms by means of a colour change arising from an interaction between the colour changing agent, metal and siderophores as released by microorganisms (e.g. bacteria). In conjunction, the surfactant component can be used to disinfect the bacteria via disruption (e.g. rupture) of bacterial cell membranes, which are composed of a phospholipid bilayer.

The intensity of the colour change is related to the amount of siderophores present, and thereby related to the levels of bacteria. As a result, a user of the composition of the present invention can determine the level of disinfection required, e.g. whether further composition should be applied and/or whether further cleaning (e.g. mechanical cleaning, such as scrubbing) is required to reduce and/or eliminate detected microorganisms.

It will be appreciated, therefore, that the compositions of the present invention facilitate cleaning. In particular, a small quantity of composition (e.g. a light spray) could be applied to an article (such as a surface) requiring cleaning, giving feedback as to whether the surface is contaminated. In the event that a colour change takes place, further composition and/or other cleaning agents can be applied to the article and/or further cleaning can take place. This can be continued until a colour change is no longer observed.

Alternatively or additionally, the composition of the present invention may be useful in applications in which detection of certain chemicals (e.g. acidic or basic chemicals) is desirable. As described above, the composition of the present invention can be sprayed onto an article (e.g. a surface) and used to detect the presence of chemicals by means of a colour change arising from an interaction between the colour changing agent, metal and chemicals present.

Generally speaking, the composition of the present invention is suitable for the detection of chemicals which alter the binding affinity of the colour changing agent for the metal such that a colour change occurs in the colour changing agent upon exposure to said chemicals.

The colour changing agent, such as CAS (e.g. CAS S) may be tetrabasic, having 4 ionizable hydrogen moieties. Ionization of one or more of said moieties may lead to a colour change. A chemical capable of achieving said ionization may therefore be detectable upon exposure to such a colour changing agent. The skilled person will understand the nature of chemicals for which the composition of the present invention suitable for detecting.

The colour changing agent may provide a change in colour in the visible spectrum (e.g. about 390 nm to 700 nm).

The metal and metal aggregation inhibitor may be present at a molar ratio of about 1:0.5 to 7; optionally about 1:0.5 to 7; optionally about 1:0.75 to 6; optionally about 1:0.75 to 5; optionally about 1:0.75 to 3; optionally about 1:1 to 2; optionally about 1:1 to 1.5; optionally about 1:1.3.

The amount of metal aggregation inhibitor should be sufficient to provide the aforementioned function to suitably hinder, restrain or prevent aggregation of the metal.

Certain metal aggregation inhibitors strongly bind to metals (e.g. iron) and hence their presence at excess levels (i.e. beyond levels required to perform its function as an aggregation inhibitor) may be undesirable. In particular, excess of such metal aggregation inhibitors may impede uptake of the metal by siderophores and/or colour changing agent and thereby impede or prevent the colour change.

The metal and colour changing agent may be present at a molar ratio of about 1:1 to 15; optionally about 1:2 to 13; optionally about 1:2 to 11.5; optionally about 1:2 to about 8; optionally about 1:2 to 5; optionally about 1:2 to 4; optionally about 1:3.3.

The amount of colour changing agent should be sufficient to provide the aforementioned function of providing a change in colour on binding and/or release of the metal.

Certain colour changing agents may stain articles (e.g. surfaces) onto which they are applied, and hence presence at excess levels (i.e. beyond levels required to perform their function) may be undesirable.

The metal and surfactant may be present at a weight ratio of about 1:500 to 7,000; optionally about 1:750 to 4,500; optionally about 1:750 to 3,000; optionally about 1:1,000 to 1,500; optionally about 1:1,200. As used herein, the weight of the iron refers to the equivalent weight of elemental iron (i.e. Fe) and not the total weight of an iron-containing compound (e.g. $FeCl_3$).

The metal and surfactant may be present at a molar ratio of about 1:25 to 240; optionally about 1:25 to 200; optionally about 1:25 to 150; optionally about 1:25 to about 100; optionally about 1:30 to about 70; optionally about 1:40 to about 60; optionally about 1:51.

The surfactant component may reduce staining of articles (e.g. articles requiring decontamination) by the colour changing agent.

The relative ratios of the iron, metal aggregation inhibitor, colour changing agent and surfactant may be tailored depending on the application.

Some surfactants strongly bind to metal (e.g. iron) in a similar way to the aggregation inhibitor noted above, and hence presence at excess levels (i.e. beyond levels required to perform its function as a surfactant for cleaning) may similarly be undesirable.

The surfactant may be hexadecyl-trimethyl-ammonium bromide (HDTMA), a polysorbate (optionally a polysorbate 80 or polysorbate 20, optionally a Tween®), an aliphatic phenol ethoxylate (such as Triton X-100; optionally wherein the aliphatic group is an alkyl group; optionally wherein the aliphatic phenol ethoxylate is octyl phenol ethoxylate), an aliphatic sulfobetaine (optionally wherein the aliphatic group is an alkyl group, optionally wherein the aliphatic group has a straight chain length of 8 to 16 carbon atoms; optionally wherein the aliphatic sulfobetaine is lauryl sulfobetaine), an aliphatic trimethylammonium bromide (optionally wherein the aliphatic group is an alkyl group, optionally wherein the aliphatic group has a straight chain length of 10 to 22 carbon atoms, optionally wherein the aliphatic trimethylammonium bromide is myristyltrimethylammonium bromide or trimethyloctadecylammonium bromide), optionally wherein the surfactant is hexadecyl-trimethyl-ammonium bromide (HDTMA).

The surfactant may be a polysorbate (optionally a polysorbate 80 [i.e. polyoxyethylene (20) sorbitan monooleate] or polysorbate 20, optionally a Tween®), an aliphatic phenol ethoxylate (such as Triton X-100; optionally wherein the aliphatic group is an alkyl group; optionally wherein the aliphatic phenol ethoxylate is octyl phenol ethoxylate), an aliphatic sulfobetaine (optionally wherein the aliphatic group is an alkyl group, optionally wherein the aliphatic group has a straight chain length of 8 to 16 carbon atoms; optionally wherein the aliphatic sulfobetaine is lauryl sulfobetaine), an aliphatic trimethylammonium bromide (optionally wherein the aliphatic group is an alkyl group, optionally wherein the aliphatic group has a straight chain length of 10 to 22 carbon atoms, optionally wherein the aliphatic trimethylammonium bromide is myristyltrimethylammonium bromide or trimethyloctadecylammonium bromide).

Certain surfactants may bind with the metal and thereby hinder or prevent metal uptake by the colour changing agent and/or siderophore. Therefore, the surfactant may be chosen so as to have a lower metal binding affinity than the colour changing agent and/or siderophore. Siderophores have a binding affinity for iron, $K_d$ of greater than about $10^{30}$ $M^{-1}$.

Suitably, the surfactant may be chosen such that the binding affinity of the siderophore is at least about 10 times higher than the surfactant; optionally at least about 50 times higher; optionally at least about 100 times higher; optionally at least about 1,000 times higher; optionally at least about 10,000 times higher; optionally at least about 100,000 times higher. Generally speaking, a higher relative binding affinity of the colour changing agent and/or siderophore (relative to the surfactant) is preferred.

Polysorbate surfactants are not believed to interact with the colour changing agent (such as CAS, e.g. CAS S).

The liquid vehicle may be water. Water may be useful in the destruction of bacterial cell membranes via formation of an emulsion comprising lipids derived from the phospholipid bilayer.

The liquid vehicle may be present at a level of about 50 ml to 1,000 ml for about 1 g of the other components in the composition (i.e. 1 g referring to the total weight of the metal, metal aggregation inhibitor, colour changing agent and surfactant); optionally about 100 ml to 800 ml for about 1 g; optionally about 200 ml to 550 ml for about 1 g; optionally about 375 ml for about 1 g.

The liquid vehicle may alternatively be present at a level of about 50 ml to 2,000 ml for about 0.1 g of the other components in the composition (i.e. 0.1 g referring to the total weight of the metal, metal aggregation inhibitor, colour changing agent and surfactant); optionally about 200 ml to 1,600 ml for about 0.1 g; optionally about 250 ml to 1,100 ml for about 0.1 g; optionally about 300 ml to 500 ml for about 0.1 g.

Diluting the composition using a liquid vehicle may be useful to reduce staining by the composition. Dilution may also assist in producing a visible colour change.

According to a second aspect of the present invention, there is provided a composition comprising:
 a metal;
 a metal aggregation inhibitor; and
 a colour changing agent;
 wherein the metal is bindable to the colour changing agent to provide a change in colour on binding and/or release thereof, and wherein the metal and colour changing agent are present at a molar ratio of about 1:1 to 15.

The composition of the second aspect of the present invention may be useful in a colour changing label for detecting the presence of and/or level of siderophores, and, by extension, microbes.

The metal and colour changing agent may be present at a molar ratio of about 1:2 to 13; optionally about 1:2 to 11.5; optionally about 1:2 to about 8; optionally about 1:2 to 5; optionally about 1:2 to 4; optionally about 1:3.3. Such a composition may be useful for incorporation into a label, and/or may be useful as a composition per se for the detection of microorganisms and/or chemicals, as discussed herein.

The metal and colour changing agent may be present at a molar ratio of about 1:1 to 20 optionally about 1:2.5 to 17.5; optionally about 1:5 to about 15; optionally about 1:7.5 to 12.5; optionally about 1:10. Such a composition may be useful for incorporation into a wipe, and/or may be useful as a composition per se for the detection of microorganisms and/or chemicals, as discussed herein.

The metal and aggregation inhibitor may be present at a molar ratio of about 1:0.5 to 7; optionally about 1:0.5 to 7; optionally about 1:0.75 to 6; optionally about 1:0.75 to 5; optionally about 1:0.75 to 3; optionally about 1:1 to 2; optionally about 1:1 to 1.5; optionally about 1:1.3. Such a composition may be useful for incorporation into a label, and/or may be useful as a composition per se for the detection of microorganisms and/or chemicals, as discussed herein.

The metal and aggregation inhibitor may be present at a molar ratio of about 1:0.5 to 30; optionally about 1:0.75 to 27.5; optionally about 1:0.75 to 25; optionally about 1:5 to 25; optionally about 1:10 to 25; optionally about 1:15 to 25; optionally about 1:17.5 to 22.5; optionally about 1:20. Such a composition may be useful for incorporation into a wipe, and/or may be useful as a composition per se for the detection of microorganisms and/or chemicals, as discussed herein.

The relative ratios of the iron, metal aggregation inhibitor and colour changing agent may be tailored depending on the application.

The composition may further comprise a liquid vehicle (optionally water). Inclusion of a liquid vehicle may facilitate application of the composition to a label.

The liquid vehicle may be present at a level of about 50 ml to 200 ml for about 1 g of the other components in the composition (i.e. 1 g referring to the total weight of the metal, metal aggregation inhibitor and colour changing agent); optionally about 75 ml to 150 ml for about 1 g; optionally about 85 ml to 130 ml for about 1 g; optionally about 100 ml for about 1 g.

The composition of the second aspect of the present invention may be a sprayable composition, comprising a liquid vehicle. Sprayable compositions may be useful in the event that detection of microorganisms and/or certain chemicals (e.g. acidic or basic chemicals) is desirable. As described above, the composition of the present invention can be sprayed onto an article (e.g. a surface) and used to detect the presence of microorganisms and/or chemicals by means of a colour change arising from an interaction between the colour changing agent, metal and chemicals present.

In the event the composition of the second aspect of the present invention is a sprayable composition, the liquid vehicle may be present at a level of about 50 ml to 2,000 ml for about 0.1 g of the metal, metal aggregation inhibitor and colour changing agent components; optionally about 200 ml to 1,600 ml for about 0.1 g; optionally about 250 ml to 1,100 ml for about 0.1 g; optionally about 300 ml to 500 ml for about 0.1 g.

The composition may further comprise a surfactant. The metal and surfactant may be present at a weight ratio of about 1:500 to 7,000; optionally about 1:750 to 4,500; optionally about 1:750 to 3,000; optionally about 1:1,000 to 1,500; optionally about 1:1,200.

The surfactant may be hexadecyl-trimethyl-ammonium bromide (HDTMA), a polysorbate (optionally a polysorbate 80 or polysorbate 20, optionally a Tween®), an aliphatic phenol ethoxylate (such as Triton X-100; optionally wherein the aliphatic group is an alkyl group; optionally wherein the aliphatic phenol ethoxylate is octyl phenol ethoxylate), an aliphatic sulfobetaine (optionally wherein the aliphatic group is an alkyl group, optionally wherein the aliphatic group has a straight chain length of 8 to 16 carbon atoms; optionally wherein the aliphatic sulfobetaine is lauryl sulfobetaine), an aliphatic trimethylammonium bromide (optionally wherein the aliphatic group is an alkyl group, optionally wherein the aliphatic group has a straight chain length of 10 to 22 carbon atoms, optionally wherein the aliphatic trimethylammonium bromide is myristyltrimethylammonium bromide or trimethyloctadecylammonium bromide), optionally wherein the surfactant is hexadecyl-trimethyl-ammonium bromide (HDTMA).

The metal and surfactant may be present at a molar ratio of about 1:25 to 240; optionally about 1:25 to 200; optionally about 1:25 to 150; optionally about 1:25 to about 100; optionally about 1:30 to about 70; optionally about 1:40 to about 60; optionally about 1:51.

Common features of the first and second aspects of the present invention are set out below.

The metal may be iron; optionally iron (III); optionally $FeCl_3$; such as hydrated $FeCl_3$ ($FeCl_3.6H_2O$).

The colour changing agent may be a chromeazurol (such as chromeazurol S or chromeazurol B) or a tannin. The colour changing agent may be chromeazurol S (CAS). Chromeazurol compounds form a blue colour upon binding with iron and are coloured orange in the absence of iron.

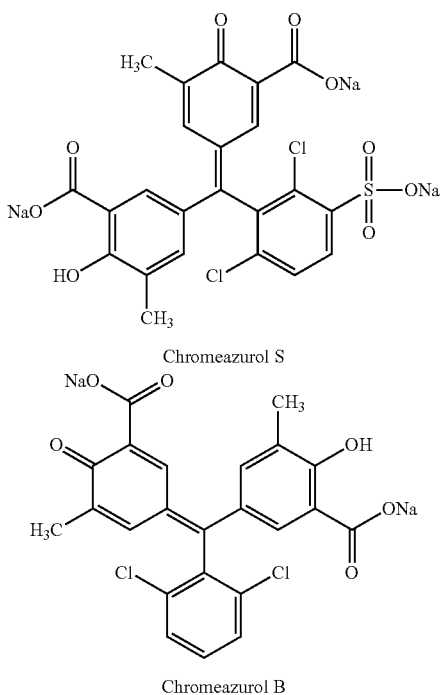

Chromeazurol S

Chromeazurol B

Tannins are a class of polyphenolic compounds, such as vescalagin, castalagin [(33beta)-isomer of vescalagin], penta-O-galloyl-beta-D-glucose.

It will be appreciated that chromeazurol compounds may exist in different isomeric forms and/or salt forms, particularly as a result of conjugation in the compounds. All such forms are envisaged herein.

The aggregation inhibitor may be an aliphatic-trimethyl-ammonium bromide; optionally wherein the aliphatic group is an alkyl group, optionally wherein the aliphatic group has a straight chain length of 12 to 22 carbon atoms; such as about 14 to 18 carbon atoms.

The aggregation inhibitor may be hexadecyl-trimethyl-ammonium bromide (HDTMA). HDTMA is particularly useful in the context of cleaning applications (e.g. a sprayable composition), since HDTMA also provides an antimicrobial effect.

HDTMA may also behave as a surfactant. In the context of the present invention, when both a surfactant metal aggregation inhibitor (e.g. HDTMA) and a surfactant are present, the metal aggregation inhibitor should be understood to define a different component to the surfactant component. In other words, the surfactant and metal aggregation inhibitor are different chemical entities.

HDTMA strongly binds to metal (e.g. iron) and hence its presence at excess levels (i.e. beyond levels required to perform its function as an aggregation inhibitor), such as levels required to provide a sufficient surfactant (cleaning) effect, may be undesirable. In particular, excess HDTMA may impede uptake of the metal by siderophores and thereby impede or prevent the colour change. The same considerations may apply to other metal aggregation inhibitors.

According to a third aspect of the present invention, there is provided substrate comprising a substrate carrier having a composition therein, wherein the composition comprises:
a metal;
a metal aggregation inhibitor; and
a colour changing agent;
wherein the metal is bindable to the colour changing agent to provide a change in colour on binding and/or release thereof.

The substrate of the present invention is useful in applications in which detection of microorganisms is desirable. The substrate can be wiped over an article (e.g. a surface) and used to detect the presence of microorganisms by means of a colour change arising from an interaction between the colour changing agent, metal and siderophores as released by microorganisms (e.g. bacteria).

Alternatively or additionally, the substrate of the present invention may be useful in applications in which detection of certain chemicals (e.g. acidic or basic chemicals) is desirable.

The intensity of the colour change is related to the amount of siderophores, and thereby related to the levels of bacteria. The intensity of the colour change is alternatively or additionally related to the amount of chemicals present. As a result, a user of the substrate of the present invention can determine the level of microorganisms and/or chemicals present with the substrate of the present invention.

The substrate carrier may be a non-woven material, such as fibrous material (optionally paper or a fabric).

The substrate carrier may comprise cellulose, polyester, lignin, protein, acrylic, nylon, aramid, polyurethane, alginate and/or mixtures thereof (such as lignocellulosic fibres). The substrate carrier may comprise fibres of cellulose, polyester, lignin and/or mixtures thereof (such as lignocellulosic fibres), optionally wherein the substrate carrier comprises cellulose.

The substrate carrier may comprise pulp, wool, silk, jute, linen, ramie, sisal, bagasse, banana fibres, hemp, flax, camel hair, kenaf and/or mixtures thereof.

The substrate may be absorbent. The substrate may be able to absorb at least about 1 times its weight (based on the total weight of the substrate) in liquid, such as at least about 2 its weight, such as at least about 3 times its weight, such as at least about 5 times its weight in liquid. The substrate may be able to absorb between about 1-10 times its weight (based on the total weight of the substrate) in liquid, such as between about 2-8 times its weight, such as between about 3-7 times its weight in liquid.

The substrate may be a wipe, such as a surface wipe or a personal (e.g. baby) wipe; a paper towel; or a tissue (such as a toilet or facial tissue). The substrate may be a surface wipe.

The composition may be as defined above in the second aspect of the present invention.

The substrate may be moistened (i.e. with liquid). The substrate may be moistened with water. The substrate may be moistened with about 0.1 to 10 times its weight (based on the total weight of the substrate) of liquid, such as about 0.25 to 7.5 times its weight of liquid, such as about 0.5 to 5 times its weight of liquid, such as about 1 to 5 times its weight of liquid.

According to a fourth aspect of the present invention, there is provided a label comprising a membrane, the membrane enveloping a composition and a carrier, the composition comprising:
a metal;
a metal aggregation inhibitor; and
a colour changing agent,
wherein the metal is bindable to the colour changing agent to provide a change in colour on binding and/or release thereof; wherein the membrane is impermeable to the colour changing agent to prevent passage therethrough, and wherein the membrane is permeable to siderophores to permit passage therethrough and to contact the colour changing agent.

The label of the present invention can be used to indicate whether microbes (e.g. bacteria) are present and/or are above a certain level. The label may be used in food and/or beverage applications, to determine whether or not the food and/or beverage are safe to consume.

By way of example, the label may be provided inside a sealed container holding meat. Over time, bacteria present in the meat will multiply, and eventually the meat will become toxic. As the bacteria multiply, the amount of sideraphores present will increase. Sideraphores will migrate through the membrane, contact the colour changing agent, sequester the metal and cause it to be released from the colour changing agent. Once the amount of sideraphores reaches a certain level, this will cause a visible change in colour of the colour changing agent, indicating that the meat is no longer safe to eat.

The permeability of the membrane prevents colour changing agent from leaching out of the label, which can cause contamination and/or discolouration (e.g. of food and/or beverage which may be provided in proximity to the label, such as in a container on which the label is to be applied). Certain colour changing agents may be toxic, and so preventing passage in this manner may be desirable to avoid toxic materials leaching out of the label (which may then contact food and/or beverage in proximity to the label). Alternatively or additionally, certain colour changing agents may cause other undesirable effects, e.g. staining, taste changes, etc. and hence such permeability of the membrane may provide advantages in this regard.

The permeability of the membrane ensures that siderophores (e.g. as released by bacteria present on food and/or beverage provided in proximity to the label) may pass through the membrane to contact the colour changing agent.

The membrane may be impermeable to the metal and/or metal aggregation inhibitor to prevent passage therethrough. As with the colour changing agent, metal and/or metal aggregation inhibitors may similarly cause contamination and/or discolouration.

The label may be configured to be applied to a food and/or beverage container (such as by bonding, e.g. adhesion, optionally in the form of a sticker; or otherwise fastening thereto).

The label may be configured such that the membrane is permeable to permit passage of siderophores through only a part of the membrane, such as a portion of the membrane for facing a food and/or beverage, in instances where the label is applied to a food and/or beverage container; and/or a portion of the membrane overlying the carrier (thereby permitting passage to the carrier). The remainder of the membrane may be substantially sealed, substantially preventing components of the composition and/or ambient materials through the membrane.

The composition in the label may be as defined above in the first or second aspects of the invention.

The membrane may be substantially transparent in the visible spectrum.

The membrane may be a size exclusion membrane; optionally sized to prevent passage of species (e.g. one or more components of the composition, such as the colour changing agent), while permitting passage of siderophores.

A size exclusion membrane may comprise pores which are sized to permit or restrict passage of species having molecular weights of varying sizes.

The size exclusion membrane may comprise pores sized to prevent passage of species having a molecular weight of about 1 kilodaltons or more; optionally about 2 kilodaltons or more; optionally about 4 kilodaltons or more; optionally about 6 kilodaltons or more; optionally about 8 kilodaltons or more; optionally about 10 kilodaltons or more; optionally about 12 kilodaltons or more; optionally about 15 kilodaltons or more. It has been unexpectedly found that size exclusion membranes with pores sized to prevent passage of components having weights above the quoted ranges, and consequently to permit passage of lower weight components, may nonetheless block such lower weight components (e.g. the colour changing agent such as CAS) from passage through the membrane. It will be appreciated that using a size exclusion membrane configured to permit passage of species of a high molecular weight means that the pore size in those membranes is relatively large. It will further be appreciated that selecting a size exclusion membrane with a large pore size may be useful for facilitating passage of siderophores through the membrane.

Without wishing to be bound by theory, it is understood that the size exclusion membrane may prevent passage of certain charged species (e.g. the colour changing agent, such as CAS), somewhat irrespective of the pore size therein. Charged membranes can repels co-ions which have the same sign charge as that of the membrane by an electric repulsive force. A charged membrane can reject ions much smaller than the membrane pore radii but not solute molecules that carry no electric charge at a similar size. Normally, membranes are negatively charged. This allows the transport of siderophores, that are generally assumed to hold no charge, but blocks the transport of CAS that holds negative electric charge.

The membrane may comprise cellulose, and/or benzoylated cellulose.

The carrier may provide a supporting structure to hold the components of the composition.

The carrier may be desiccated. A desiccated carrier may be useful for providing a concentration gradient and thereby promoting migration of siderophores through the membrane. The desiccated carrier may provider an increased drive for absorption of water and, therefore, bacterial siderophore. This may give an increased catchment area for the label.

Suitably, the desiccated carrier may have a liquid (e.g. water) content of less than about 20% on a weight basis; optionally less than about 15%; optionally less than about 10%; optionally less than about 5%; optionally less than about 2.5%; optionally about 0%.

In applications involving a dessicated carrier, the composition may conveniently be applied to the carrier as a liquid and the carrier thereafter dessicated.

The carrier may be selected from agar, polyvinylalcohol, polyvinylchloride, gelatin, cellulose, pectin, ethylene vinyl alcohol polymer, polyurethane, polystyrene, methoxyl pectin gels, modified starch/wheat fibre gel, acyl gellan gum (optionally a high acyl gellan gum, such as high acyl Kelcogel®), a linear sulphated polysaccharides (such as carrageenan).

The label may be for use with food and/or beverages. Food or beverage articles have particular requirements from a health and safety perspective, particularly in relation to toxicity. Thus, suitability for use in this regard should be understood to mean that the label meets such requirements.

According to a fifth aspect of the present invention there is provided a food and/or beverage container comprising a label according to the fourth aspect.

Features described above in relation to the first, second, third, fourth and/or fifth aspects of the present invention also represent features of the each other aspect of the present invention (and vice versa) subject to a technical incompatibility that would prevent such a combination of features. Furthermore, it will be evident to the skilled person that advantages set out above in respect of the first, second, third, fourth and/or fifth aspects of the present invention are also offered by each other aspect of the present invention (again and vice versa).

The invention will now be further described, by way of example only, with reference to the accompanying examples and FIGURE, in which:

FIG. 1 shows an emission spectrum for CAS at variable pH.

EXAMPLES

Example 1

Stock solutions of compositions in accordance with the present invention were prepared by mixing the following solutions:

Stock Solution A:
  50 ml of a solution comprising 0.06 g CAS in 50 ml $H_2O$;
  9 ml of a solution comprising 0.0027 g hydrated $FeCl_3$ ($FeCl_3.6H_2O$) in 10 ml 10 mM HCl;
  8 ml of a solution comprising 0.0146 g HDTMA in 8 ml $H_2O$; and
  33 ml of a solution comprising 2 g Tween® 80 in 33 ml $H_2O$ Stock Solution B:
  50 ml of a solution comprising 0.06 g CAS in 50 ml $H_2O$;
  9 ml of a solution comprising 0.0081 g hydrated $FeCl_3$ ($FeCl_3.6H_2O$) in 10 ml 10 mM HCl;
  8 ml of a solution comprising 0.0146 g HDTMA in 8 ml $H_2O$; and
  33 ml of a solution comprising 2 g Tween® 80 in 33 ml $H_2O$ 10 ml of each stock solution were diluted with 90 ml water to provide compositions for use as a cleaning spray.

10 ml of each stock solution were diluted with 10 ml of water to provide compositions for use in a label. Compositions may be added to the label by mixing with the carrier (e.g. agar) at a temperature of about 40° C.

Example 2

A range of tests were performed to investigate the colouring effect of increasing molar ratio of iron relative to CAS S (hydrated $FeCl_3$ ($FeCl_3.6H_2O$) to CAS S). The results were as follows:

1:0.0099 [1000×]—Blue
1:0.099 [100×]—Blue
1:0.485 [50×]—Blue
1:0.99 [10×]—Blue
1:9.9 [1×]—Pale Blue
1:19.8 [0.5×]—Red
1:99 [0.1×]—Red
1:198 [0.05×]—Red A deep blue colour was obtained with a ratio of 1:3.3.

Example 3

Stock solution B was diluted by a factor of two to yield a solution for visibility testing. The solution was then made to the following dilutions, with the resulting qualitative visibility:

1×—dark blue, very little changes to orange seen with bacteria
2×—dark blue, still hard to see changes to orange with bacteria
5×—dark to medium blue, adding bacteria you can visibly see a grey and orange
10×—medium blue, mixing with bacteria shows a transparent orange colour
20×—near transparent blue, difficult to see orange colour because of high transparency
50×—almost completely clear with a hint blue Testing was performed in a 50 ml falcon tube with each dilution at a volume of 10 ml. 1 ml of OD 1 Bacteria (*E-coli* BL21 (DE3) cells and grown to an optical density of 1 as determined using UV-VIS) in water was added to each dilution to a final volume of 11 ml. The dilutions were placed at a volume of 1 ml on white weighing boats.

Example 4

Membrane testing was performed with 10 kDa MWCO dialysis tubing. Dialysis tubing was cut to 10 cm in length to form a cylinder of tubing open and both ends. After tying one end of the dialysis tubing, the formulation was added to 5 ml total volume and then the second end was tied off to prevent any leaking of the formulation from the ends of the tubing.

The membrane with the formulation was put into milk at room temperature for 24 hours. The results were compared with adding 5 ml total volume directly to the milk and also compared relative to a control which comprised of the membrane filled with 5 ml of water. No observable colour change occurred in the milk when the membrane was used. The formulation inside the membrane did change colour from blue to orange indicating that detection of siderophores was still possible.

Example 5

An exemplary composition suitable for inclusion in a substrate, such as a surface wipe, is given below.

| | Weight (g) | Molar mass | Moles |
|---|---|---|---|
| Chromeazurol S | 0.03 | 605.28 | 4.96E−04 |
| Iron(III) chloride hexahydrate | 0.00135 | 270.3 | 4.99E−05 |
| (1-hexadecyl)trimethylammonium bromide | 0.0365 | 364.45 | 1.00E−03 |

0.0008475 g of the composition was mixed with 12.25 mL water and then doped into a 10×10 cm cellulose wipe.

Example 6

An experiment was conducted to demonstrate the effect of pH on the colour of compositions in accordance with the present invention. A series of compositions having pH between 0.8 and 12.8 were prepared in accordance with the following procedure.

Preparatory solutions with a pH between 0.8 and 6.8 were prepared from a stock solution comprising hydrochloric acid (1 mL, 37%) in distilled water (50 mL) and then diluted with sufficient further distilled water to yield solutions having a pH level 0.3 units lower than that intended for the final compositions for testing (e.g. where the final composition for testing was intended to have a pH of 1.8, then the preparatory solution was prepared by diluting the stock solution with further distilled water to a pH of 1.5).

Preparatory solutions with a pH between 7.8 and 12.8 were prepared from a stock solution comprising sodium hydroxide (0.4 g) in distilled water (50 mL) and then diluted with further distilled water to yield solutions having a pH level 0.3 units higher than that intended for the final compositions for testing.

Preparatory solutions were then diluted 1:1 (volume) with a water-mixed composition prepared in accordance with Example 5, to yield final compositions for testing having the desired pH.

The (unbuffered) final compositions for testing were observed to have colouring as set out in the table below.

| pH | Colour |
|---|---|
| 0.8 | Red |
| 1.8 | Blue |
| 2.8 | Blue |
| 3.8 | Blue |
| 4.8 | Blue |
| 5.8 | Blue |
| 6.8 | Blue |
| 7.8 | Blue |
| 8.8 | Blue |
| 9.8 | Blue |
| 10.8 | Orange |
| 11.8 | Yellow |
| 12.8 | Green |

A light absorbance study was conducted (Nanodrop 2000 Spectrophotometer, 0.1 mm path length) on the final compositions for testing to determine absorbance of CAS at 458 nm ($\lambda_{max}$ absorption for CAS S) at variable pH between 1 and 13. The results are shown in FIG. 1.

The invention claimed is:

1. A composition comprising:
    a metal;
    a metal aggregation inhibitor; and
    a colour changing agent;
    wherein the metal is bindable to the colour changing agent to provide a change in colour on binding and/or release thereof,
    wherein the metal and colour changing agent are present at a molar ratio of about 1:1 to 20, and
    wherein the metal and aggregation inhibitor are present at a molar ratio of about 1:0.5 to 30.

2. The composition according to claim 1, wherein the metal and colour changing agent are present at a molar ratio of about 1:2 to 13.

3. The composition according to claim 1, wherein the metal and aggregation inhibitor are present at a molar ratio of about 1:0.5 to 7.

4. The composition according to claim 1, wherein the metal and aggregation inhibitor are present at a molar ratio of about 1:5 to 25.

5. The composition according to claim 1, wherein the composition is sprayable, comprising a liquid vehicle.

6. The composition according to claim 5, wherein the liquid vehicle is present at a level of about 50 ml to 1,000 ml for about 0.1 g of the metal, metal aggregation inhibitor and colour changing agent components.

7. The composition according to claim 1, further comprising a surfactant.

8. The composition according to claim 7, wherein the metal and surfactant are present at a weight ratio of about 1:500 to 7,000.

9. The composition according to claim 7, wherein the surfactant is hexadecyl-trimethyl-ammonium bromide (HDTMA), a polysorbate, an aliphatic phenol ethoxylate, an aliphatic sulfobetaine, or an aliphatic trimethylammonium bromide.

10. The composition according to claim 1, wherein the metal is iron.

11. The composition according to claim 1, wherein the colour changing agent is a chromeazurol or a tannin.

12. The composition according to claim 1, wherein the colour changing agent is chromeazurol S (CAS).

13. The composition according to claim 1, wherein the aggregation inhibitor is an aliphatic-trimethyl-ammonium bromide.

14. The composition according to claim 1, wherein the aggregation inhibitor is hexadecyl-trimethyl-ammonium bromide (HDTMA).

15. A substrate comprising a substrate carrier having a composition therein, wherein the composition comprises:
 a metal;
 a metal aggregation inhibitor; and
 a colour changing agent;
 wherein the metal is bindable to the colour changing agent to provide a change in colour on binding and/or release thereof; and
 wherein the metal and aggregation inhibitor are present at a molar ratio of about 1:0.5 to 30.

16. The substrate according to claim 15, wherein the substrate carrier is a non-woven material.

17. The substrate according to claim 15, wherein the substrate carrier comprises cellulose, polyester, lignin, protein, acrylic, nylon, aramid, polyurethane, alginate and/or mixtures thereof.

18. The substrate according to claim 15, wherein the substrate carrier comprises cellulose, polyester, lignin and/or mixtures thereof.

19. The substrate according to claim 15, wherein the substrate carrier comprises pulp, wool, silk, jute, linen, ramie, sisal, bagasse, banana, hemp, flax, camel hair, kenaf and/or mixtures thereof.

20. The substrate according to claim 15, wherein the substrate is absorbent.

21. The substrate according to claim 15, wherein the substrate is a wipe, a paper towel; or a tissue.

22. The substrate according to claim 15, wherein the substrate is moistened.

23. The substrate according to claim 15, wherein the metal is iron.

24. The substrate according to claim 15, wherein the colour changing agent is a chromeazurol or a tannin.

25. The substrate according to claim 15, wherein the colour changing agent is chromeazurol S (CAS).

26. The substrate according to claim 15, wherein the aggregation inhibitor is an aliphatic-trimethyl-ammonium bromide.

27. The substrate according to claim 15, wherein the aggregation inhibitor is hexadecyl-trimethyl-ammonium bromide (HDTMA).

28. A sprayable composition comprising:
 a metal;
 a metal aggregation inhibitor;
 a colour changing agent;
 a surfactant; and
 a liquid vehicle;
 wherein the metal is bindable to the colour changing agent to provide a change in colour on binding and/or release thereof;
 wherein the metal and aggregation inhibitor are present at a molar ratio of about 1:0.5 to 30.

29. The sprayable composition according to claim 28, wherein the metal and aggregation inhibitor are present at a molar ratio of about 1:0.5 to 7.

30. The sprayable composition according to claim 28, wherein the metal and colour changing agent are present at a molar ratio of about 1:1 to 15.

31. The sprayable composition according to claim 28, wherein the metal and surfactant are present at a weight ratio of about 1:500 to 7,000.

32. The sprayable composition according to claim 28, wherein the surfactant is hexadecyl-trimethyl-ammonium bromide (HDTMA), a polysorbate, an aliphatic phenol ethoxylate, an aliphatic sulfobetaine, or an aliphatic trimethylammonium bromide.

33. The sprayable composition according to claim 28, wherein the surfactant is a polysorbate, an aliphatic phenol ethoxylate, an aliphatic sulfobetaine, or an aliphatic trimethylammonium bromide.

34. The sprayable composition according to claim 28, wherein the liquid vehicle is water.

* * * * *